ated Esters and Acids

United States Patent [19]
Petrzilka

[11] 4,234,741
[45] Nov. 18, 1980

[54] PROCESS FOR THE PREPARATION OF γ, δ-UNSATURATED ESTERS AND ACIDS

[75] Inventor: Martin Petrzilka, Puplinge, Switzerland

[73] Assignee: Firmenich, S.A., Geneva, Switzerland

[21] Appl. No.: 67,025

[22] Filed: Aug. 16, 1979

[30] Foreign Application Priority Data

Aug. 30, 1978 [CH] Switzerland .................... 9136/78

[51] Int. Cl.$^3$ ..................... C07C 51/00; C07C 163/00
[52] U.S. Cl. ................................. 560/211; 562/599; 260/410.9 R; 260/413; 260/550
[58] Field of Search ................. 560/211; 562/599; 260/607 R, 410.9 R, 413

[56] References Cited
PUBLICATIONS

March, Advanced Organic Chemistry, pp. 1052, 1053, (1977).
Fiesen et al., Reagents for Organic Synthesis, pp. 520, 521, (1975).

*Primary Examiner*—Robert Gerstl
*Attorney, Agent, or Firm*—Scully, Scott, Murphy & Presser

[57] ABSTRACT

A process is disclosed for the preparation of γ,δ-unsaturated esters and acids starting from an alkylvinyl ether and an allylic alcohol. The process makes use of a benzene-selenenyl halide as critical reagent.

10 Claims, No Drawings

PROCESS FOR THE PREPARATION OF γ,δ-UNSATURATED ESTERS AND ACIDS

SUMMARY OF THE INVENTION

The present invention relates to a process for the preparation of a compound of formula

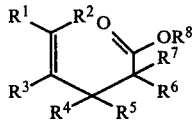
(I)

wherein symbols $R^1$ to $R^8$ are identical or different and each represents a hydrogen atom or an alkyl radical, which process comprises the following subsequent steps:

a. reacting an alkyl-vinyl ether of formula

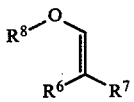
(II)

with a benzene-selenenyl halide, b. adding to the thus obtained reaction mixture an allylic alcohol of formula

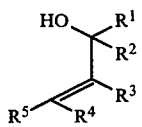
(III)

to give an acetal of formula

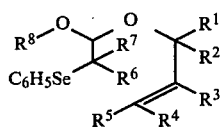
(IV)

c. oxidizing said acetal to give the compound of formula

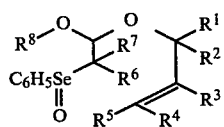
(V)

d. subjecting oxide (V) thus obtained to a intramolecular thermal rearrangement to give the desired ester of formula (I) wherein $R^8$ represents an alkyl radical and e. saponifying said ester to yield the corresponding γ,δ-unsaturated acid.

The present invention relates further to compounds of formula

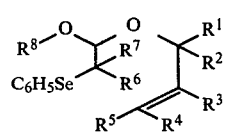
(IV)

wherein symbols $R^1$ to $R^8$ have the same meaning as given for formula (I) above.

A further object of the invention is to provide compounds of formula

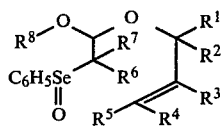
(V)

wherein symbols $R^1$ to $R^8$ have the same meaning as given for formula (I) above.

BACKGROUND OF THE INVENTION

The great variety of aliphatic esters and acids which find current use in the industry of flavours and perfumes includes certain γ,δ-unsaturated derivatives, some of which are natural occurring. Acids such as pent-4-enoic, hept-4-enoic and 3-methyl-dec-4-enoic have found a particularly advantageous utilization as flavouring ingredients. Among the ester derivatives, special mention should be made for ethyl hept-4-enoate and ethyl oct-4-enoate in their trans isomeric configuration, which compounds have been found to occur in a fraction extracted from passion fruit.

Very numerous are the synthesis known sofar for the preparation of the said compounds and recent investigations have shown the applicability of the Claisen rearrangement to the synthesis of γ,δ-unsaturated acids and esters. For instance, Johnson [see: W. S. Johnson et al., J.Am.Chem.Soc., 92, 741 (1970)] has described the preparation of unsaturated esters starting from an allylic alcohol and an alkyl ortho-acetate according to the following reaction scheme:

Scheme I

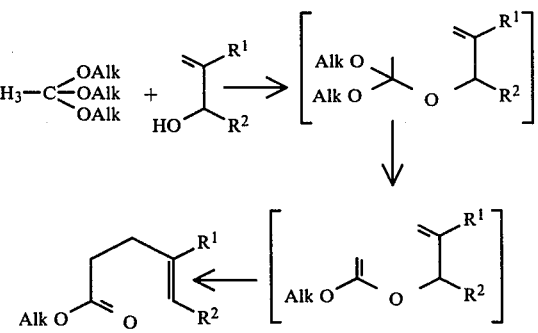

Alk=alkyl
$R^1$, $R^2$=H, alkyl

Another process developed by Ireland [See: R. E. Ireland et al., J.Am.Chem.Soc., 94, 5897 (1972), and Tetrahedron Letters 1975, 3975] has recourse to the principle of the rearrangement of an allylic ester enolate, which enolate is formed in situ starting from an allylic ester in accordance with the following reaction scheme.

Scheme II

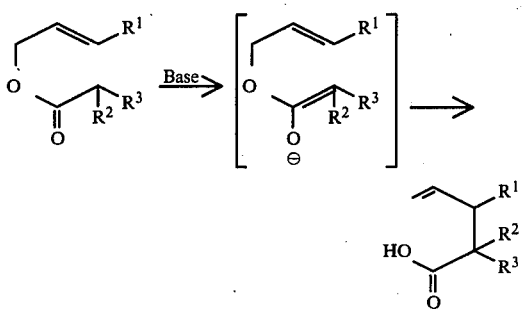

$R^1$, $R^2$, $R^3$ = alkyl

The present invention provides a novel and original solution to the problem of preparing γ,δ-unsaturated acids and esters.

THE INVENTION

The process of the invention is illustrated by the following reaction scheme:

Scheme III

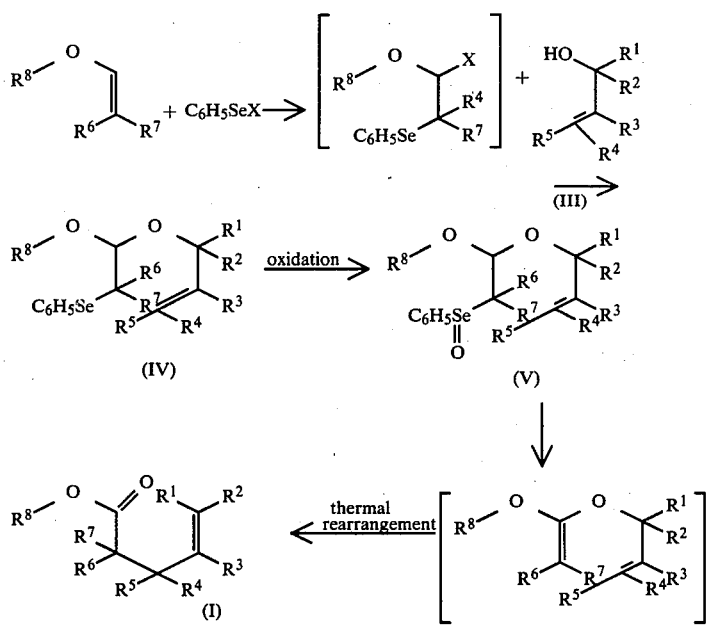

X = halogen

The addition of the benzene-selenenyl halide to the alkyl-vinyl ether (II) can be preferably effected in the presence of a polar organic solvent, such as an ether, e.g. diethyl ether or tetrahydrofuran or a chlorinated hydrocarbon such as dichloromethane. A preferred benzene-selenenyl halide is benzene-selenenyl bromide.

The subsequent step, which consists in the addition of allylic alcohol (III) to the reaction mixture, occurs in the presence of an organic base, preferably a nitrogen organic base such as an amine. Preferred amines include diisopropylamine, dicyclohexylamine or hexylamine. The subsequent steps of oxidation and intramolecular rearrangement can be effected according to usual techniques [see: D. L. J. Clive, Tetrahedron, 34, 1049 and ff. (1978)]. Thus, compounds (IV) can be converted into their corresponding oxidized derivatives by means of an alkali metal periodate, a peracid or hydrogen peroxide. Contrary to other oxidized alkyl selenenyl derivatives which do not possess a heteroatom in the β-position, compounds (V) have been found to be particularly stable, no decomposition has been observed after prolonged storage, even at room temperature. The thermal rearrangement which characterizes the last step of the process of the invention is carried out by subjecting oxide (V) to the action of heat, for instance in an inert organic medium.

According to a preferred embodiment of the process of the invention, oxide (V), in suspension in an aromatic hydrocarbon, such as xylene, more particularly m-xylene, was refluxed in the presence of n-hexylamine until complete elimination of benzene-selenenic acid and formation of the desired ester of formula (I).

For practical reasons, the choice of the reaction temperature in this last step depends on the chosen solvent. Preferred temperatures are of from about 100° and about 150° C.

It has become apparent that the presence of n-hexylamine reduced the formation of by-products and consequently enabled an appreciable improvement of the yield of the final product.

Of course, the esters of formula (I) thus obtained can easily be converted into their corresponding acids by direct saponification, for example in a basic medium.

As an exemplification we indicate hereinbelow some of the acids obtained in accordance of the process of the invention:

pent-4-enoic acid,
3-methyl-pent-4-enoic acid,
4-methyl-pent-4-enoic acid,
hex-4-enoic acid and
5-methyl-hex-4-enoic acid.

Compounds (II) and (III), as well as the benzene-selenenyl reagent used in the invention process, are either commercial products, or products which can easily be prepared in accordance with current methods.

The invention is illustrated by but not limited to the following example wherein the temperature is indicated in degrees centigrade.

EXAMPLE

Ethyl 4-methyl-pent-4-en-1-oate 1.65 Mole-equivalents of ethyl-vinyl ether have been added at 25° to a solution of 1.5 Mole-equivalents of benzene-selenenyl bromide in 10 ml of anhydrous tetrahydrofuran, then a solution of 1 Mole-equivalent of β-methallyl alcohol and 1.65 Mole-equivalents of diisopropylamine in 2 ml of anhydrous tetrahydrofuran was rapidly added to the reaction mixture kept under vigorous stirring. This addition provoked the formation of a white voluminous precipitate, whereupon the mixture was left under stirring for 10 supplementary minutes and poured then in an aqueous solution of $NaHCO_3$ and extracted with ether.

The combined organic extracts were subjected to the usual treatments of washing (water and an aqueous NaCl solution), drying over $K_2CO_3$ and concentration at reduced pressure. A purification carried out by means of column chromatography on alumina (activity III), eluent:hexane/ether (8/1) enabled the separation of a compound of formula

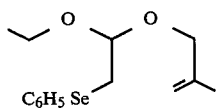

with a 99% yield. This purification eliminates diphenyl diselenide. The analytical characteristics of the obtained product were the following:

IR ($CHCl_3$): 1650, 1580, 1479, 1380, 1345, 910, 690 cm$^{-1}$;

NMR ($CDCl_3$, 100 MHz): 1.20 (3H, t, J=6.5); 1.77 (3H, s); 3.15 (2H, d, J=6); 3.46–3.80 (2H, m); 4.00 (2H); 4.78 (1H, t, J=6); 4.90 (1H); 5.00 (1H); 7.14–7.35 (3H, m); 7.44–7.66 (2H, m) δ ppm;

MS: 300 and 298 (M+), 255, 229, 211, 183, 171, 157, 129, 92, 55 (100%).

The subsequent oxidation of the compound thus obtained was carried out by treating it at 25° during 1 h with a mixture of 1.5 Mole-equivalent of sodium periodate and 1.1 Mole-equivalent of $NaHCO_3$ in an alcoholic mixture of methanol and water (6:1).

The oily viscous oxide obtained was colorless and showed the following characteristics:

IR ($CHCl_3$): 1651, 1580, 1480, 1380, 1345, 910, 820, 735 cm$^{-1}$;

NMR ($CDCl_3$, 100 MHz): 1.09–1.38 (3H, m); 1.72 and 1.80 (3H, 2s); 3.19 (2H, d, J=5.5); 3.38–4.16 (4H, m); 4.78–5.08 (3H, m); 7.66–7.90 (2H, m) δ ppm;

MS: 300 and 298 (M+−16), 271, 255, 229, 211, 183, 171, 145, 129, 91, 55 (100%).

This product was finally subjected to a thermal rearrangement by refluxing it for 4 h in m-xylene (b.p. 139°) in the presence of n-hexylamine (3 Mole-equivalents) and magnesium sulphate (500 mg/mMole).

Ethyl 4-methyl-pent-4-enoate was thus obtained in a yield of 96%. This ester was directly saponified in a 2 N aqueous solution of KOH to give the corresponding acid, 4-methyl-pent-4-enoic acid.

IR ($CHCl_3$): 1710, 1650, 900 cm$^{-1}$;

NMR ($CDCl_3$): 1.75 (3H, s); 2.20–2.66 (4H, m); 4.64–4.84 (2H, m); 10.33 (1H) δ ppm;

MS: 114 (M+), 91, 69, 60, 55 (100%), 41.

By replacing in the example above β-methallylalcohol by one of the following allylic alcohols, it was possible to obtain a series of γ,δ-unsaturated acids and esters. The table below summarizes the results obtained.

| Starting allylic alcohol | Obtained acid | Yield* |
|---|---|---|
| OH⌇⌇ | 1. ⌇⌇COOH | 78% |
| HO⌇⌇ | 2. ⌇⌇COOH | 95% |
| HO⌇⌇ | 3. ⌇⌇COOH | 80% |
| HO⌇⌇ | 4. ⌇⌇COOH | 96% |
| HO⌇⌇ | 5. ⌇⌇COOH | 100% |

*Calculated on the basis of the selenium oxide derivative.

Their analytical data were the following:

1. Pent-4-enoic acid

IR ($CHCl_3$): 1708, 1648, 923 cm$^{-1}$;

NMR ($CDCl_3$): 2.44; 4.90–5.22 (2H, m); 5.63–6.08 (1H, m); 11.41 (1H, s) δ ppm;

MS: 100 (M+), 91, 55 (100%), 41.

2. 3-Methyl-pent-4-enoic acid

IR ($CHCl_3$): 1708, 1643, 922 cm$^{-1}$;

NMR ($CDCl_3$): 1.13 (3H, d, J=6); 2.30–2.51 (2H, m); 2.51–2.92 (1H, m); 4.89–5.24 (2H, m); 5.86 (1H, dxdxd, J=17, 10 and 6.5); 10.71 δ ppm;

MS: 114 cM+), 99, 91, 69, 55 (100%), 41.

3. Hex-trans 4-enoic acid

IR ($CHCl_3$): 1710, 975 cm$^{-1}$;

NMR ($CDCl_3$): 1.67 (3H, d, J=4); 2.16–2.58 (4H, m); 5.40–5.60 (2H, m); 10.50 (1H) δ ppm;

MS: 114 (M+), 99, 96, 73, 68, 60, 55 (100%), 41.

5. 5-Methyl-hex-4-enoic acid

IR ($CHCl_3$): 1708, 1655, 1040, 831 cm$^{-1}$;

NMR ($CDCl_3$): 1.63 and 1.70 (6H, 2s); 2.38 (4H); 5.02–5.29 (1H); 10.43 (1H) δ ppm;

MS: 128 (M+), 92, 91, 69, 65, 51, 41, 39 (100%).

As it has been shown for the preparation of hex-trans 4-enoic acid, the process of the invention enables the synthesis of γ, δ-unsaturated acids and esters wherein the γ,δ double bond is in its trans isomeric form; the intramolecular thermal rearrangement is therefore eminently stereospecific.

What I claim is:

1. A process for the preparation of a compound of formula

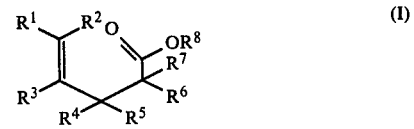

wherein symbols $R^1$ to $R^7$ are identical or different and each represents a hydrogen atom or an alkyl radical and $R^8$ is an alkyl radical, which comprises the following subsequent steps:

a. reacting an alkyl-vinyl ether of formula

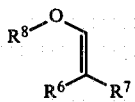  (II)

with a benzene-selenenyl halide, b. adding to the thus obtained reaction mixture an allylic alcohol of formula

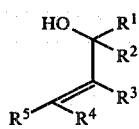  (III)

to give an acetal of formula

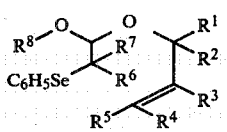  (IV)

c. oxidizing said acetal to give the compound of formula

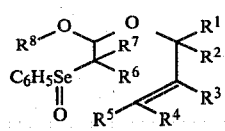  (V)

and, d. subjecting oxide (V) thus obtained to an intramolecular thermal rearrangement to give the desired ester of formula (I) wherein $R^8$ represents an alkyl radical.

2. Process according to claim 1, wherein the addition of the benzeneselenenyl halide to the alkyl-vinyl ether is effected in the presence of a polar organic solvent.

3. Process according to claim 2, wherein the benzeneselenenyl halide is benzene-selenenyl bromide.

4. Process according to claim 1, wherein the intramolecular thermal rearrangement is carried out in an inert organic solvent and at a temperature in the vicinity of the boiling point of the chosen solvent.

5. Process according to claim 4, wherein the inert organic solvent is m-xylene.

6. Process according to claim 1, wherein the ester of formula (I) is saponified to yield the corresponding $\gamma,\delta$-unsaturated acid.

7. A compound of formula

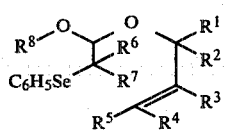  (IV)

wherein symbols $R^1$ to $R^8$ have the same meaning as given for formula (I) in claim 1.

8. The compound of claim 7, wherein $R_1$, $R_2$, $R_4$, $R_5$, $R_6$ and $R_7$ are hydrogen; $R_3$ is methyl; and $R_8$ is ethyl.

9. A compound of formula

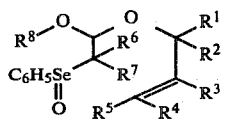  (V)

wherein symbols $R^1$ to $R^8$ have the same meaning as given for formula (I) in claim 1.

10. The compound of claim 9 wherein $R_1$, $R_2$, $R_4$, $R_5$, $R_6$ and $R_7$ are hydrogen; $R_3$ is methyl; and $R_8$ is ethyl.

* * * * *